US00PP26518P2

(12) United States Plant Patent
Braeunig

(10) Patent No.: US PP26,518 P2
(45) Date of Patent: Mar. 15, 2016

(54) ***GAURA* PLANT NAMED 'FLORGAURE'**

(50) Latin Name: *Gaura lindheimeri*
Varietal Denomination: Florgaure

(71) Applicant: Tobias Braeunig, Quedlinburg (DE)

(72) Inventor: Tobias Braeunig, Quedlinburg (DE)

(73) Assignee: Florensis B.V., Hendrik-Ido-Ambacht (NL)

( * ) Notice: Subject to any disclaimer, the term of this patent is extended or adjusted under 35 U.S.C. 154(b) by 227 days.

(21) Appl. No.: 13/999,003

(22) Filed: Dec. 31, 2013

(51) Int. Cl.
*A01H 5/02* (2006.01)

(52) U.S. Cl.
USPC ..... Plt./432

(58) Field of Classification Search
USPC ..... Plt./432, 263.1
See application file for complete search history.

*Primary Examiner* — Susan McCormick Ewoldt
*Assistant Examiner* — Karen Redden
(74) *Attorney, Agent, or Firm* — C. A. Whealy

(57) ABSTRACT

A new and distinct cultivar of *Gaura* plant named 'Florgaure', characterized by its compact, upright and outwardly spreading plant habit; moderately vigorous growth habit; freely basal branching habit; greyed red-colored stems; dark green to brown-colored leaves; freely flowering habit; red purple-colored flowers; and good garden performance.

1 Drawing Sheet

Botanical designation: *Gaura lindheimeri*.
Cultivar denomination: 'FLORGAURE'.

BACKGROUND OF THE INVENTION

The present invention relates to a new and distinct cultivar of *Gaura* plant, botanically known as *Gaura lindheimeri* and hereinafter referred to by the name 'Florgaure'.

The new *Gaura* is a product of a planned breeding program conducted by the Inventor in Quedlinburg, Germany. The objective of the breeding program is to create new compact *Gaura* plants with attractive leaf and flower coloration.

The new *Gaura* plant originated from an open-pollination during the summer of 2010 in Quedlinburg, Germany of a proprietary selection of *Gaura lindheimeri* identified as code number 3199, not patented, as the female, or seed, parent with an unknown selection of *Gaura lindheimeri* as the male, or pollen, parent. The new *Gaura* plant was discovered and selected by the Inventor as a single flowering plant from within the progeny of the stated open-pollination in a controlled environment in Quedlinburg, Germany during the spring of 2011.

Asexual reproduction of the new *Gaura* plant by vegetative cuttings in a controlled environment in Hendrik-Ido-Ambacht, The Netherlands since the summer of 2011 has shown that the unique features of this new *Gaura* plant are stable and reproduced true to type in successive generations.

SUMMARY OF THE INVENTION

Plants of the new *Gaura* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Florgaure'.

These characteristics in combination distinguish 'Florgaure' as a new and distinct *Gaura* plant:

1. Compact, upright and outwardly spreading plant habit.
2. Moderately vigorous growth habit.
3. Freely basal branching habit.
4. Greyed red-colored stems.
5. Dark green to brown-colored leaves.
6. Freely flowering habit.
7. Red purple-colored flowers.
8. Good garden performance.

Plants of the new *Gaura* can be compared to plants of the female parent selection. Plants of the new *Gaura* differ from plants of the female parent selection in the following characteristics:

1. Plants of the new *Gaura* are more compact than plants of the female parent selection.
2. Plants of the new *Gaura* are more freely branching and denser than plants of the female parent selection.
3. Leaves of plants of the new *Gaura* are dark green to brown in color whereas leaves of plants of the female parent selection are brown to red in color.
4. Plants of the new *Gaura* and the female parent selection differ in flower color as plants of the female parent selection have dark rose-colored flowers.

Plants of the new *Gaura* can also be compared to plants of *Gaura lindheimeri* 'Whirling Butterflies', not patented. In side-by-side comparisons conducted in Hendrik-Ido-Ambacht, The Netherlands, plants of the new *Gaura* differed from plants of 'Whirling Butterflies' in the following characteristics:

1. Plants of the new *Gaura* were more compact than plants of 'Whirling Butterflies'.
2. Plants of the new *Gaura* were more freely branching and denser than plants of 'Whirling Butterflies'.
3. Leaves of plants of the new *Gaura* were dark green to brown in color whereas leaves of plants of 'Whirling Butterflies' were light green in color.

4. Plants of the new *Gaura* and 'Whirling Butterflies' differed in flower color as plants of 'Whirling Butterflies' had light rose-colored flowers.

Plants of the new *Gaura* can also be compared to plants of *Gaura lindheimeri* 'Gaudros', disclosed in U.S. Plant Pat. No. 18,279. In side-by-side comparisons conducted in Hendrik-Ido-Ambacht, The Netherlands, plants of the new *Gaura* differed from plants of 'Gaudros' in the following characteristics:

1. Plants of the new *Gaura* were more freely branching and denser than plants of 'Gaudros'.
2. Plants of the new *Gaura* and 'Gaudros' differed in flower color as plants of 'Gaudros' had light pink-colored flowers.

BRIEF DESCRIPTION OF THE PHOTOGRAPH

The accompanying colored photograph illustrates the overall appearance of the new *Gaura* plant showing the colors as true as it is reasonably possible to obtain in colored reproductions of this type. Colors in the photograph may differ slightly from the color values cited in the detailed botanical description which accurately describe the colors of the new *Gaura* plant.

The photograph comprises a side perspective view of a typical plant of 'Florgaure' grown in a container.

DETAILED BOTANICAL DESCRIPTION

The aforementioned photograph and following observations, measurements and values describe plants grown during the spring in 13-cm containers in an outdoor nursery in Hendrik-Ido-Ambacht, The Netherlands and under cultural practices typical of commercial *Gaura* production. During the production of the plants, day temperatures ranged from 13° C. to 23° C., night temperatures ranged from 7° C. to 13° C. and light levels averaged 6,000 lux. Plants were pinched one time and were 15 weeks old when the photograph and description were taken. In the following description, color references are made to The Royal Horticultural Society Colour Chart, 1995 Edition, except where general terms of ordinary dictionary significance are used.

Botanical classification: *Gaura lindheimeri* 'Florgaure'.

Parentage:

*Female, or seed, parent*.—Proprietary selection of *Gaura lindheimeri* identified as code number 3199, not patented.

*Male or pollen parent*.—Unknown selection of *Gaura lindheimeri*, not patented.

Propagation:

*Type*.—By vegetative cuttings.

*Time to initiate roots, summer*.—About two weeks at temperatures about 13° C. to 23° C.

*Time to initiate roots, winter*.—About three weeks at temperatures about 13° C. to 23° C.

*Time to produce a rooted young plant, summer*.—About five weeks at temperatures about 13° C. to 23° C.

*Time to produce a rooted young plant, winter*.—About six weeks at temperatures about 13° C. to 23° C.

*Root description*.—Fine, fibrous; white in color.

*Rooting habit*.—Freely branching; medium density.

Plant description:

*Plant and growth habit*.—Herbaceous perennial; compact, upright and outwardly spreading plant habit; broad inverted triangle; freely basal branching habit with about 30 lateral branches developing per plant, pinching enhances lateral branch development; dense and bushy plant form; moderately vigorous growth habit.

*Plant height*.—About 17 cm.

*Plant diameter*.—About 30 cm.

Lateral branch description:

*Length*.—About 15 cm to 20 cm.

*Diameter*.—About 2.5 mm.

*Internode length*.—About 1.5 cm.

*Strength*.—Strong.

*Aspect*.—Upright to outwardly spreading.

*Texture*.—Sparsely pubescent.

*Color*.—Close to 182A and 191A.

Leaf description:

*Arrangement*.—Alternate; simple.

*Length*.—About 1.5 cm to 6 cm.

*Width*.—About 3 mm to 7 mm.

*Shape*.—Lanceolate.

*Apex*.—Acute.

*Base*.—Attenuate.

*Margin*.—Shallowly lobed.

*Texture, upper surface*.—Sparsely pubescent.

*Texture, lower surface*.—Smooth, glabrous.

*Venation pattern*.—Pinnate.

*Color*.—Developing leaves, upper and lower surfaces: Close to 185A; towards the apex, close to 147A. Fully expanded leaves, upper surface: Close to 147A; venation, close to 185A. Fully expanded leaves, lower surface: Close to 147B; venation, close to 185B.

*Petioles*.—Length: About 3 mm. Diameter: About 0.1 mm. Texture, upper and lower surfaces: Smooth, glabrous. Color, upper and lower surfaces: Close to 147A.

Flower description:

*Flower arrangement and habit*.—Single flowers arranged on upright terminal spicate racemes; freely flowering habit with about 15 flowers per inflorescence; flowers face upright to outwardly.

*Fragrance*.—Faintly fragrant, pleasant.

*Natural flowering season*.—Plants flower continuously from April to November in northwestern Europe; plants begin flowering about four to five weeks after planting rooted cuttings.

*Flower longevity*.—Individual flowers last about three to four days on the plant; flowers not persistent.

*Inflorescence height*.—About 17 cm.

*Inflorescence diameter*.—About 5 cm.

*Flower diameter*.—About 2.5 cm to 2.8 cm.

*Flower depth (height)*.—About 1.4 cm to 1.6 cm.

*Flower buds*.—Length: About 5 mm to 15 mm. Diameter: About 1 mm. Shape: Tubular. Color: Close to 183A.

*Petals*.—Arrangement: Four in a single whorl. Length: About 1.2 cm. Width: About 6 mm. Shape: Oblanceolate. Apex: Rounded. Base: Attenuate. Margin: Entire. Texture, upper and lower surfaces: Smooth, glabrous. Color: When opening, upper and lower surfaces: Close to 63A. Fully opened, upper and lower surfaces: Close to 63A.

*Sepals*.—Arrangement: Four in a single whorl. Length: About 2 cm. Width: About 2 mm. Shape: Narrowly lanceolate; reflexed. Apex: Acute. Base: Attenuate. Margin: Entire. Texture, upper and lower surfaces: Smooth, glabrous. Color, upper and lower surfaces: Close to 59C.

*Pedicels*.—Length: About 2 cm. Diameter: About 2 mm. Strength: Strong. Texture: Sparsely pubescent. Color: Close to 187B.

*Reproductive organs*.—Stamens: Quantity: Eight per flower. Filament length: About 1 cm. Filament color: Close to 63B. Anther shape: Lanceolate. Anther length: About 3 mm. Anther color: Close to 59A. Pollen amount: Scarce. Pollen color: Close to 4B. Pistils: Quantity: One per flower. Pistil length: About 2 cm. Style length: About 1.2 cm. Style color: Close to 185C. Stigma shape: Four-parted. Stigma color: Close to 157A. Ovary color: Close to 59A. Seeds and fruits: Seed and fruit development have not been observed on plants of the new *Gaura*.

Garden performance: Plants of the new *Gaura* have been observed to have good garden performance and tolerate wind, rain and temperatures ranging from about −10° C. to about 35° C.

Pathogen & pest resistance: Plants of the new *Gaura* have not been observed to be resistant to pathogens and pests common to *Gaura* plants.

It is claimed:

1. A new and distinct *Gaura* plant named 'Florgaure' as illustrated and described.

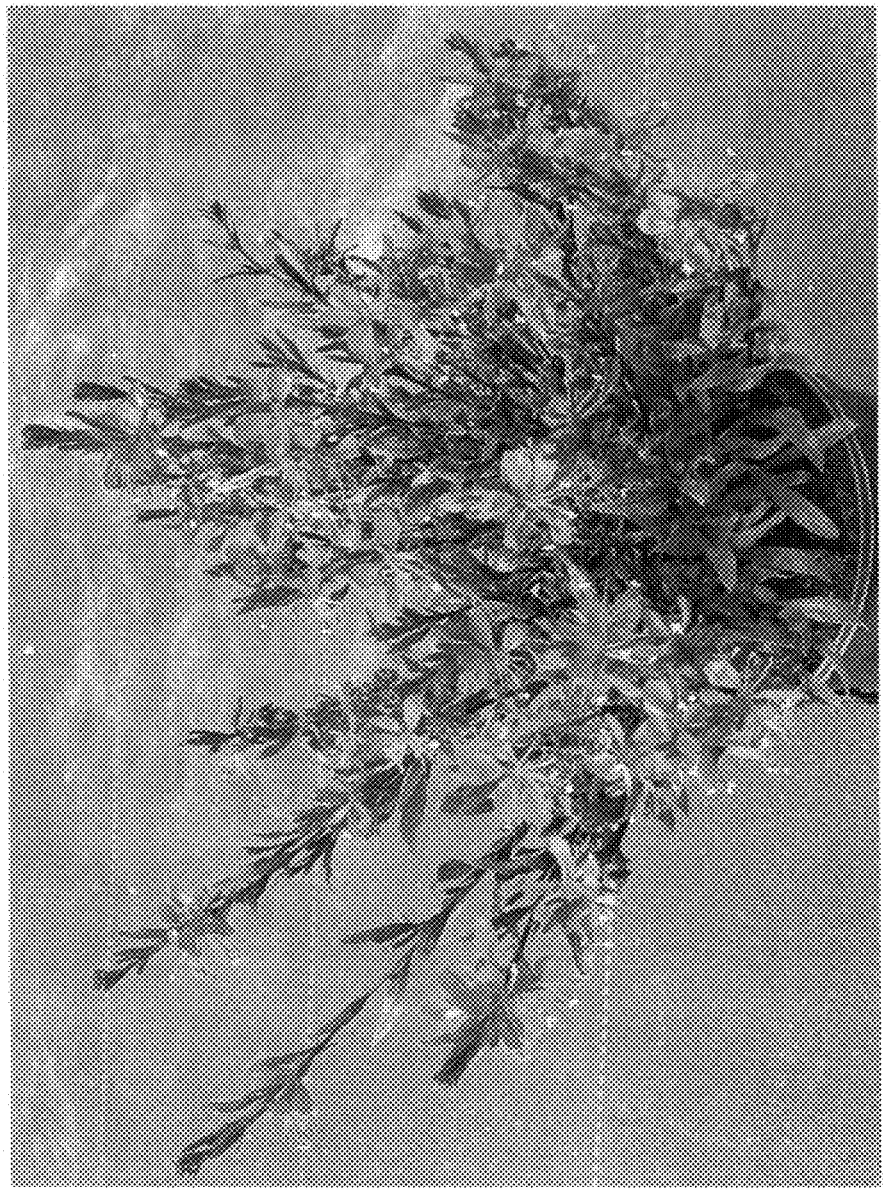

* * * * *